United States Patent [19]

Blum et al.

[11] Patent Number: 5,189,176

[45] Date of Patent: Feb. 23, 1993

[54] BIS-OXAZOLIDINES, OXAZOLIDINE MIXTURES CONSISTING ESSENTIALLY THEREOF AND THEIR USE AS HARDENERS FOR PLASTICS PRECURSORS CONTAINING ISOCYANATE GROUPS

[75] Inventors: Harald Blum, Wachtendonk; Josef Pedain, Cologne; Karl-Heinz Hentschel, Bergisch Gladbach, all of Fed. Rep. of Germany

[73] Assignee: Bayer Aktiengesellschaft, Leverkusen, Fed. Rep. of Germany

[21] Appl. No.: 723,863

[22] Filed: Jul. 1, 1991

[30] Foreign Application Priority Data

Jul. 7, 1990 [DE] Fed. Rep. of Germany ....... 4021659

[51] Int. Cl.$^5$ ............................................. C07D 263/04
[52] U.S. Cl. ................................... 548/215; 525/375
[58] Field of Search ......................................... 548/215

[56] References Cited

U.S. PATENT DOCUMENTS

| | | | |
|---|---|---|---|
| 3,661,923 | 5/1972 | Emmons et al. | 548/215 |
| 3,962,271 | 6/1976 | Sipi | 548/215 |
| 4,002,601 | 1/1977 | Hajek et al. | 548/215 |
| 4,002,637 | 1/1977 | Lewis | 548/215 |
| 4,138,545 | 2/1979 | Emmons | 548/215 |
| 4,975,493 | 12/1990 | Blum et al. | 525/375 |

FOREIGN PATENT DOCUMENTS

| | | |
|---|---|---|
| 260339 | 3/1988 | European Pat. Off. . |
| 329375 | 2/1989 | European Pat. Off. . |
| 2018033 | 2/1972 | Fed. Rep. of Germany . |
| 2590571 | 5/1987 | France ................. 548/215 |

OTHER PUBLICATIONS

Parrinello et al. Chem. Abstr. vol 14, entry 421237j (1990).
Brooks et al. Chem. Abstr. vol. 112 entry 100810p (1989).
Blum et al. Chem. Abstr. vol. 111 entry 80051r (1989).

*Primary Examiner*—Donald G. Daus
*Attorney, Agent, or Firm*—Joseph C. Gil; Thomas W. Roy

[57] ABSTRACT

The present invention relates to bis-oxazolidines corresponding to formula (II)

$$\begin{array}{c} CH_2-CH_2 \\ | \quad\quad | \\ O \quad\quad N-(CH_2)_2-O-CO-NH-(CH_6)_2- \\ \backslash\;/ \\ CH \\ | \\ R \end{array} \quad (II)$$

$$\begin{array}{c} CH_2-CH_2 \\ | \quad\quad | \\ -NH-CO-O-(CH_2)_2-N \quad\quad O \\ \backslash\;/ \\ CH \\ | \\ R \end{array}$$

wherein R represents a branched, saturated, aliphatic hydrocarbon radical containing 5 to 8 carbon atoms.

The present invention also relates to oxazolidine mixtures, which are also suitable as hardeners for plastics precursors containing isocyanate groups, consisting essentially of a) bis-oxazolidines corresponding to formula (II) above and b) 0.03 to 0.3 moles per mole of component (a), of compounds corresponding to formula (III)

$$\begin{array}{c} CH_2-CH_2 \\ | \quad\quad | \\ HO-CH_2-CH_2-N \quad\quad O \\ \backslash\;/ \\ CH \\ | \\ R \end{array}$$

wherein R represents a saturated, branched, aliphatic hydrocarbon radical containing 5 to 8 carbon atoms.

The present invention additionally relates to a process for the production of these oxazolidine mixtures and to their use in combination with polymer precursors containing isocyanate groups for coating or sealing compositions.

2 Claims, No Drawings

BIS-OXAZOLIDINES, OXAZOLIDINE MIXTURES CONSISTING ESSENTIALLY THEREOF AND THEIR USE AS HARDENERS FOR PLASTICS PRECURSORS CONTAINING ISOCYANATE GROUPS

BACKGROUND OF THE INVENTION

1. Field of the Invention

This invention relates to new, liquid bis-oxazolidines, to mixtures containing these oxazolidines, to a process for their production and to their use as hardeners for plastics precursors containing isocyanate groups.

2. Description of the Prior Art

Compounds containing oxazolidine structural units I

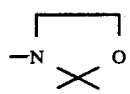
(I)

which will be referred to hereinafter simply as oxazolidines, have the property of splitting back into the starting components, hydroxyamine and carbonyl compound, for example under the effect of atmospheric moisture.

Accordingly, compounds such as these are potential reactants for polymer precursors containing isocyanate groups, in particular organic polyisocyanates or isocyanate prepolymers. DE-PS 2,446,438 describes oxazolidines containing urethane groups which are free from ester groups and, accordingly, show increased stability to hydrolysis, particularly in the alkaline range. These oxazolidines may be mixed with isocyanate prepolymers based on aliphatic diisocyanates to form one-component formulations which shown high stability in storage and which cure in the presence of moisture to form crosslinked coatings.

Oxazolidines based on bis-hydroxyamines and aldehydes may be easily produced and show a balanced ratio of reactivity and stability in storage.

However, the aldehyde-based oxazolidines described in DE-PS 2,446,438, particularly those used in the examples, are still attended by certain disadvantages, namely:

The oxazolidines mentioned have a pronounced tendency to change into a crystalline state during storage which presents considerable problems when it comes to storage, transport and application. Accordingly, either solvents have to be added, which is undesirable on ecological and economic grounds, or the products have to be stored above room temperature, i.e. in heated rooms, which is also a considerable practical disadvantage.

The oxazolidines mentioned have viscosities of more than 15,000 mPa.s at room temperature, such that reactive diluents and/or volatile solvents often have to be used during their production and during processing of the coating compositions produced therefrom.

The known oxazolidines mentioned contain readily volatile aldehydes which can lead to unwelcome emissions during the application of corresponding formulations on account of their high volatility and their pungent odor.

It has now surprisingly been found that the bis-oxazolidines containing urethane groups according to the invention and mixtures containing these oxazolidines, which are both described in detail hereinafter, are not attended by any of these disadvantages. The bis-oxazolidines and oxazolidine mixtures according to the present invention are low viscosity, solvent-free products which may be processed without a pungent odor emission, show no tendency towards crystallization, even after storage at low temperatures, and are eminently suitable as hardeners for polymer precursors containing isocyanate groups.

SUMMARY OF THE INVENTION

The present invention relates to bis-oxazolidines corresponding to formula (II)

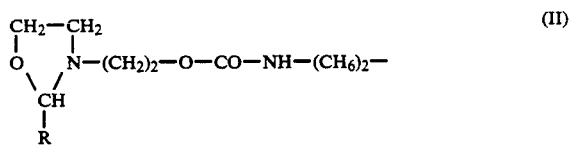
(II)

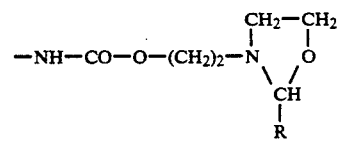

wherein R represents a branched, saturated, aliphatic hydrocarbon radical containing 5 to 8 carbon atoms.

The present invention also relates to oxazolidine mixtures, which are also suitable as hardeners for plastics precursors containing isocyanate groups, consisting essentially of a) bis-oxazolidines corresponding to formula (II) above and b) 0.03 to 0.3 moles per mole of component (a), of compounds corresponding to formula (III)

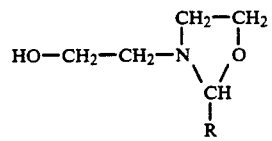

wherein R represents a saturated, branched, aliphatic hydrocarbon radical containing 5 to 8 carbon atoms.

The present invention additionally relates to a process for the production of these oxazolidine mixtures by i) reacting diethanolamine with 1.01 to 1.5 moles, per mole of diethanolamine, of an aldehyde corresponding to formula (IV)

(IV)

at 60° to 160° C., optionally in the presence of an entraining agent, to form a monohydroxyoxazolidine corresponding to formula (III) and removing the excess aldehyde and entraining agent by distillation after the reaction, and (ii) reacting 1,6-diisocyanatohexane with 2.03 to 2.3 moles, per mole of 1,6-diisocyanatohexane, of the oxazolidine corresponding to formula (III) and obtained in the first step until no more isocyanate groups can be detected in the reaction mixture.

Finally, the present invention relates to coating or sealing compositions containing these oxazolidine mixtures and polymer precursors containing isocyanate groups.

DETAILED DESCRIPTION OF THE INVENTION

Starting materials for the production of the hydroxyethyl oxazolidines corresponding to formula (III) are diethanolamine and aldehydes corresponding to formula (IV) wherein R is a saturated, branched, aliphatic hydrocarbon radical containing 5 to 8, preferably 7 carbon atoms. Suitable aldehydes corresponding to formula (IV) include 2-ethyl hexanal, 2-methyl pentanal, 2,3-dimethyl pentanal, 2-methyl heptanal, 2-methyl hexanal and 2-ethyl pentanal; 2-ethyl hexanal is particularly preferred.

To prepare the hydroxyethyl oxazolidines corresponding to formula (III), the components are generally reacted using an excess of aldehyde in a molar ratio of aldehyde to diethanolamine of 1.01:1 to 1.5:1, preferably 1.02:1 to 1.15:1.

The elimination of water which takes place during the reaction may be carried out with the aid of suitable entraining agents such as isooctane, cyclohexane, toluene, xylene and aliphatic and aromatic hydrocarbons, although excess aldehyde may also serve as the entraining agent.

The elimination of water is normally carried out at temperatures of 60° to 160° C., optionally under a light vacuum (for example 15 to 200 mbar), until the theoretical quantity of water has been substantially or completely eliminated.

Entraining agent and excess blocking agent (aldehyde) are then removed from the reaction mixture by application of a vacuum (for example 10 to 100 mbar).

If the quality of the product has to meet particularly stringent requirements in regard to color value and purity, the oxazolidine intermediate may also be purified by distillation. The products boil at about 90° to 120° C. at a pressure of 0.5 to 2.5 mbar.

In the second step of the process according to the present invention, the oxazolidine intermediate obtained, i.e., hydroxyethyl oxazolidine corresponding to formula (III), is reacted with 1,6-diisocyanatohexane at a molar ratio of hydroxyethyl oxazolidine to 1,6-diisocyanatohexane of 2.03:1 to 2.3:1, preferably 2.04:1 to 2.22:1.

The oxazolidine mixtures according to the present invention are formed during this reaction. These mixtures essentially contain the bisoxazolidines of formula (II) and, to a lesser extent, excess hydroxyethyl oxazolidine corresponding to formula (III). The mixtures contain 0.03 to 0.3 moles, preferably 0.04 to 0.22 moles, of hydroxyethyl oxazolidine (III) per mole bis-oxazolidine (II).

The reaction in the second step of the process according to the present invention is generally carried out at a temperature of 50° to 100° C. and may optionally be accelerated by the addition of suitable catalysts such as dibutyl tin oxide or dibutyl tin dilaurate.

Substantially pure bis-oxazolidines (II) according to the present invention may be obtained either by removal of the excess hydroxyethyl oxazolidine (III) by distillation or by using equivalent quantities of the starting materials in the second step of the process according to the present invention. However, the small excess of hydroxyethyl oxazolidine (III) in the mixtures does not affect their use in accordance with the invention. Accordingly, the process according to the present invention is preferably carried out using the above-mentioned excess of hydroxyethyl oxazolidine (III) to ensure that the resulting reaction product is free from isocyanate groups.

If all of the diethanolamine is not completely consumed in the first reaction step of the process according to the present invention, the hydroxyethyl oxazolidine of formula (III) used in the second step may still contain small quantities of diethanolamine. These small quantities can generally be tolerated because they react with the diisocyanate used in the second step to form ureas which, by virtue of their low concentration, do not affect the usefulness of the oxazolidine mixtures according to the present invention. However, since the first step of the process according to the present invention is generally carried out until the elimination of water is complete, the oxazolidine mixtures according to the present invention are substantially free from such secondary products.

The oxazolidine mixtures according to the present invention generally have a viscosity of less than 8,000, preferably less than 6,500 mPa.s at 23° C. and, thus, are suitable as solventless hardeners for polymer precursors containing isocyanate groups. In combination with polymer precursors containing isocyanate groups, they are suitable for the production of solventless or low solvent, one-component systems which, in turn, are suitable as binders for high quality paints, coating compositions or sealing compositions. These systems are generally cured after application by exposure to atmospheric moisture. Polymer precursors containing isocyanate groups which are suitable for the production of these systems include the organic polyisocyanates or isocyanate prepolymers described, e.g., DE-PS 2,446,438 (U.S. Pat. No. 4,002,601, herein incorporated by reference).

In the use according to the present invention, the bis-oxazolidines of formula (II) or the oxazolidine mixtures according to the present invention may also be used in admixture with analogous bis-oxazolidines which have been obtained by reaction of hydroxyethyl oxazolidines corresponding to formula (III) with diisocyanates other than 1,6-diisocyanatohexane. Mixtures such as these may be obtained when 1,6-diisocyanatohexane is replaced with mixtures of this diisocyanate with other diisocyanates and these mixtures are analogously used in the process according to the present invention. Other diisocyanates which may be used for this purpose are preferably diisocyanates containing aliphatically or cycloaliphatically bound isocyanate groups such as isophorone diisocyanate, dodecamethylene diisocyanate, tetramethylene diisocyanate, 1,4-diisocyanatocyclohexane and 2,4'-and/or 4,4'-diisocyanatodicyclohexane methane; however, aromatic diisocyanates, such as 2,4- and/or 2,6-diisocyanatotoluene, may also be used. These other diisocyanates may be present in quantities of up to 50 mole percent, based on the total quantity of diisocyanates used. The percentage of the analogous bis-oxazolidines, based on the other diisocyanates just mentioned, may obviously be correspondingly high. However, the of mixtures containing these analogous bis-oxazolidines instead of the bis-oxazolidines according to the present invention is not preferred.

EXAMPLES

All reactions were carried out in an inert gas atmosphere (nitrogen).

EXAMPLE 1a)

1,260 g (12 moles) diethanolamine and 738 g isooctane were introduced into a 4 liter reaction vessel equipped with a stirrer, cooling and heating system and water separator. 1,690 g (13.2 moles) 2-ethyl hexanal were then added over a period of 1 hour. The reaction mixture was heated on a water separator until 212 g water (theoretical: 216 g) had been eliminated. Excess 2-ethyl hexanal and isooctane were then distilled off at 70° C./approx. 10 torr.

Hydroxyethyl oxazolidine 1a), which corresponds to formula (III) when R is 1-ethyl pentyl, was obtained.

EXAMPLE 1b)

678.9 g (3.15 moles) of hydroxyethyl oxazolidine 1a) were introduced into a reaction vessel and, after heating to 90° C., 247 g (1.47 moles) 1,6-diisocyanatohexane were added. The reaction mixture was then stirred until the NCO band could no longer be seen in the IR spectrum.

An oxazolidine mixture according to the present invention was obtained in the form of a light yellow liquid having a viscosity at 23° C. of 4,300 mPa.s. The main component consisted of a bis-oxazolidine of formula (II) according to the present invention when R is 1-ethyl pentyl.

EXAMPLE 2b)

716.7 g (3.33 moles) of hydroxyethyl oxazolidine 1a) were reacted with 252 g (1.5 moles) 1,6-diisocyanatohexane as described in Example 1b). An oxazolidine mixture 2b) according to the present invention was thus obtained in the form of a light yellow liquid having a viscosity of 3,500 mPa.s at 23° C.

EXAMPLE 3b)

657.9 g (3.06 moles) of hydroxyethyl oxazolidine 1a) were reacted with 252 g (1.5 moles) 1,6-diisocyanatohexane as described in Example 1b).

An oxazolidine mixture 3b) according to the present invention was obtained in the form of a light yellow liquid having a viscosity of 5,200 mPa.s at 23° C.

EXAMPLE 4b)

502 g (2.33 moles) of hydroxyethyl oxazolidine 1a) were reacted with 141.6 g (0.84 moles) 1,6-diisocyanatohexane and 46.6 g (0.21 moles) isophorone diisocyanate as described in Example 1b).

In addition to a bis-oxazolidine of formula (II) according to the present invention, the oxazolidine mixture obtained also contained an analogous bis-oxazolidine of isophorone diisocyanate in a quantity corresponding to the quantity of isophorone diisocyanate. The product was a light yellow liquid having a viscosity of 7,800 mPa.s at 23° C.

COMPARISON EXAMPLE 5

Corresponding to Example 1 of DE-PS 2,446,438.

159 g (1.0 moles) of a hydroxyethyl oxazolidine, which corresponds to formula (III) when R is isopropyl), was obtained from diethanolamine and isobutyraldehyde and was then reacted with 84 g (0.5 moles) 1,6-diisocyanatohexane after the addition of 0.1 g tin(II) octoate.

A bis-oxazolidine, which does not correspond to the present invention, was obtained in the form of a light yellow liquid having a viscosity of 14,500 mPa.s at 23° C.

COMPARISON EXAMPLE 6

324.4 g (2.04 moles) of the hydroxyethyl oxazolidine described in Comparison Example 5 were reacted with 168 g (1.0 mole) 1,6-diisocyanatohexane to form a light yellow liquid having a viscosity of 11,300 mPa.s at 23° C.

COMPARISON EXAMPLE 7a)

174 g (1.66 moles) diethanolamine, 94 g isooctane and 200 g (1.82 moles) tetrahydrobenzaldehyde were reacted as described in Example 1a) to form hydroxyethyl oxazolidine 7a).

COMPARISON EXAMPLE 7b)

201 g (1.02 moles) of hydroxyethyl oxazolidine 7a) were reacted with 84 g (0.5 moles) 1,6-diisocyanatohexane to form a bis-oxazolidine which corresponds to formula (II) when R is cyclohexenyl and, thus, does not correspond to the present invention. The bis-oxazolidine was in the form of a light brown liquid having a viscosity of more than 100,000 mPa.s at 23° C.

COMPARISON EXAMPLE 8a)

420 g (4 moles) diethanolamine, 170 g isooctane and 431 g (4.4 moles) cyclohexanone were reacted as described in Example 1a to form a hydroxyethyl oxazolidine 8a).

COMPARISON EXAMPLE 8b)

377.5 g (2.04 moles) of hydroxyethyl oxazolidine 8a) were reacted with 168 g (1.0 mole) 1,6-diisocyanatohexane as described in Example 1b) to form bis-oxazolidine 8b) which does not correspond to the present invention. The bis-oxazolidine was in the form of a light yellow liquid having a viscosity of 90,000 mPa.s at 23° C.

The oxazolidine mixtures according to the present invention had viscosities of 3,500 to 7,800 mPa.s at 23° C. and, therefore, were eminently suitable for the production of solventless coating compositions. The products prepared in accordance with Comparison Examples 5) and 6) with viscosities of 11,300 to 14,500 mPa.s were limited in processability because of their higher viscosities.

Due to their high viscosities of ≧90,000 mPa.s, the products obtained in accordance with Comparison Examples 7) and 8) were not suitable for the production of solventless coatings.

STORABILITY TESTS

The oxazolidine mixtures prepared in accordance with Examples 1) to 4) and Comparison Examples 5) and 6) were stored in sealed containers at room temperature (20°–25° C.) and at 3° C. The following results were obtained:

| | Storage at: | |
|---|---|---|
| | Room temperature | 3° C. |
| Ex. 1 | liquid after 12 months | liquid after 12 months |
| Ex. 2 | liquid after 12 months | liquid after 12 months |
| Ex. 3 | liquid after 12 months | liquid after 12 months |

| | Storage at: | |
|---|---|---|
| | Room temperature | 3° C. |
| Ex. 4 | liquid after 12 months | liquid after 12 months |
| Ex. 5 | crystallized after 2-3 months | crystallized after 1 week |
| Ex. 6 | crystallized after 2-3 months | crystallized after 1 week |

In contrast to the comparison products, the oxazolidine mixtures according to the present invention were stable in storage and could be immediately processed without the need for reliquification, even after prolonged storage at low temperatures.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A bis-oxazolidine corresponding to formula (II)

$$\begin{array}{c} CH_2-CH_2 \\ | \quad\quad | \\ O \quad N-(CH_2)_2-O-CO-NH-(CH_6)_2- \\ \diagdown / \\ CH \\ | \\ R \end{array}$$ (II)

$$-NH-CO-O-(CH_2)_2-N \begin{array}{c} CH_2-CH_2 \\ | \quad\quad | \\ \quad\quad O \\ \diagdown / \\ CH \\ | \\ R \end{array}$$

wherein R represents 1-ethyl pentyl.

2. An oxazolidine mixture which is suitable as a hardener for polymer precursors containing isocyanate groups which comprises
a) a bis-oxazolidine corresponding to formula (II)

$$\begin{array}{c} CH_2-CH_2 \\ | \quad\quad | \\ O \quad N-(CH_2)_2-O-CO-NH-(CH_6)_2- \\ \diagdown / \\ CH \\ | \\ R \end{array}$$ (II)

$$-NH-CO-O-(CH_2)_2-N \begin{array}{c} CH_2-CH_2 \\ | \quad\quad | \\ \quad\quad O \\ \diagdown / \\ CH \\ | \\ R \end{array}$$

and
b) 0.03 to 0.3 moles, per mole of component a), of a compound corresponding to formula (III)

$$HO-CH_2-CH_2-N \begin{array}{c} CH_2-CH_2 \\ | \quad\quad | \\ \quad\quad O \\ \diagdown / \\ CH \\ | \\ R \end{array}$$

wherein R represents 1-ethyl pentyl.

* * * * *